US00PP17349P2

(12) United States Plant Patent
Oudshoorn

(10) Patent No.: US PP17,349 P2
(45) Date of Patent: Jan. 9, 2007

(54) ***PAPAVER* PLANT NAMED 'MATADOR'**

(50) Latin Name: *Papaver orientale*
Varietal Denomination: Matador

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 4 days.

(21) Appl. No.: 11/141,531

(22) Filed: May 31, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A distinct cultivar of *Papaver* plant name 'Matador', characterized by its upright and relatively compact plant habit; moderately vigorous growth habit; freely flowering habit; and large flowers with clear red-colored petals.

1 Drawing Sheet

Botanical designation: *Papaver orientale.*
Cultivar denomination: 'Matador'.

BACKGROUND OF THE INVENTION

The present Invention relates to a new and distinct cultivar of *Papaver* plant, botanically known as *Papaver orientale*, commercially referred to as Oriental Poppy, and hereinafter referred to by the cultivar name Matador.

The new *Papaver* is a product of a planned breeding program conducted by the Inventor in Rijpwetering, The Netherlands. The objective of the breeding program is to develop new *Papaver* cultivars with compact plant habit and numerous flowers.

The new *Papaver* originated from a cross-pollination made by the Inventor in 2000 of two unnamed selections of *Papaver orientale*, not patented. The new *Papaver* was discovered and selected by the Inventor in 2001 in a controlled environment in Rijpwetering, The Netherlands, from the resultant progeny of the stated cross-pollination on the basis of its compact plant habit, double flowers and flower color.

Asexual reproduction of the new cultivar by cuttings at Rijpwetering, The Netherlands since 2001, has shown that the unique features of this new *Papaver* are stable and reproduced true to type in successive generations.

SUMMARY OF THE INVENTION

Plants of the cultivar Matador have not been observed under all possible environmental conditions. The phenotype may vary somewhat with variations in environment such as temperature and light intensity without, however, any variance in genotype.

The following traits have been repeatedly observed and are determined to be the unique characteristics of 'Matador'. These characteristics in combination distinguish 'Matador' as a new and distinct *Papaver* cultivar:

1. Upright and relatively compact plant habit.
2. Moderately vigorous growth habit.
3. Freely flowering habit.
4. Large single flowers with clear red-colored petals.

Plants of the cultivar Matador differ from plants of the parent selections and other *Papaver* cultivars known to the Inventor, such as the cultivar Sturmfackel, not patented, in plant height as plants of the new *Papaver* are more compact than plants of the parent selections and other cultivars known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph at the top of the sheet comprises a close-up view of a typical flower of 'Matador'.

The photograph at the bottom of the sheet is a close-up view of a typical leaf of 'Matador'.

DETAILED BOTANICAL DESCRIPTION

In the following description, color references are made to The Royal Horticultural Society Colour Chart, 2001 Edition, except where general terms of ordinary dictionary significance are used. Plants used for the abovementioned photographs and following observations and measurements were grown in an outdoor nursery in Roelofarendsveen, The Netherlands, and under conditions which closely approximate commercial production conditions during the spring and summer. The photographs, measurements and observations were taken during June when the plants were about one year old. During this time, day temperatures ranged from 14 to 27° C. and night temperatures ranged from 7 to 16° C.

Botanical classification: *Papaver orientale* cultivar Matador.
Parentage:

*Female, or seed, parent.*—Unnamed selection of *Papaver orientale*, not patented.

*Male, or pollen, parent.*—Unnamed selection of *Papaver orientale*, not patented.

Propagation:

*Type.*—By cuttings.

*Time to develop roots.*—About 90 days at 18° C.

*Root description.*—Fleshy, thick; light brown to white in color.

Plant description:

*Form.*—Herbaceous perennial flowering plant; mostly upright; narrow inverted triangle. Basally branching, rosette; flowering stems arise from the base. Moderately vigorous.

*Plant height.*—About 54 cm.

*Plant diameter.*—About 43 cm.

*Foliage description.*—Arrangement: Alternate; simple. Shape: Lanceolate, pinnately and deeply dissected. Length: About 26.7 cm. Width: About 7.9 cm. Leaf segment shape: Lanceolate; mid-section and base, pinnatisect; apex, pinnatifid. Leaf segment apex: Acute. Leaf segment base: Cuneate. Leaf segment margin: Serrate. Texture, upper and lower surfaces: Pubescent; very rough. Venation pattern: Pinnate. Color: Developing foliage, upper surface; 137A. Developing foliage, lower surface: 138A. Fully expanded foliage, upper surface: 137A. Fully expanded foliage, lower surface: 137D. Venation, upper surface: 138C to 138D. Venation, lower surface: 143B. Petioles: Length: Basal leaves, About 18 cm; stem leaves, about 1.2 cm. Diameter: About 7 mm. Color: 144B.

Flower description:

*Flower type and habit.*—Single rotate flowers; flowers terminal and face mostly upright. Flowers not persistent. One flower per flowering stem.

*Natural flowering season.*—Plants flower continuously from June to early July in The Netherlands.

*Fragrance.*—None detected.

*Flower longevity on the plant.*—About three days.

*Flower size.*—Diameter: About 12.3 cm. Depth (height): About 6.1 cm.

*Flower buds.*—Length: About 3.9 cm. Diameter: About 2.6 cm. Shape: Ovoid. Texture: Pubescent; rough. Color: 143B to 143C.

*Petals.*—Arrangement/appearance: Rotate; about six petals forming a cup-shaped corolla. Length: About 7.8 cm. Width: About 7.6 cm. Shape: Broadly obovate. Apex: Rounded to irregular praemorse; ruffled. Margin: Entire; ruffled. Texture, upper and lower surfaces; Smooth; glabrous. Color: When opening and fully opened, upper surface: 42A; towards the base, 45A; basal spots, 202A. When opening and fully opened, lower surface: 42A to 43A; towards the base, 45A; basal spots, 202A.

*Sepals.*—Quantity: About four. Length: About 3.7 cm. Width: About 1.4 cm. Shape: Narrowly oblong. Apex: Acute. Margin: Serrate. Texture, upper and lower surfaces: Densely pubescent. Color, upper surface: Between 137A and 143A. Color, lower surface: 137D.

*Flowering stems* (*peduncles*).—Length: About 47.9 cm. Diameter: About 7 mm. Internode length: About 9.8 cm. Strength: Strong. Aspect: Erect. Texture: Pubescent; rough. Color: 144A to 144B.

*Reproductive organs.*—Stamens: Quantity per flower: Numerous, typically about 250. Stamen length: About 1.8 cm. Anther shape: Narrowly oblong; basifixed. Anther length: About 3 mm. Anther color: N187A. Filament length: About 1.5 cm. Filament color: 187A; towards the base, 155D. Pollen amount: Scarce. Pollen color: Between 197A and 202A. Pistils: Quantity per flower: About 13. Pistil length: About 8 mm. Stigma shape: Narrowly oblong, flat. Stigma color: Between 186A and 200A. Ovary color: 143B.

*Fruits.*—Quantity per flower: One. Type: Capsule. Length: About 3.6 cm. Diameter: About 2.9 cm. Color: 136A to 137A.

*Seeds.*—Quantity per fruit: About 900. Length: About 1 mm. Diameter: About 1 mm. Color: Closest to 202A to 202B.

Disease/pest resistance: Plants of the new *Papaver* have not been noted to be resistant to pathogens and pests common to *Papaver*.

Temperature tolerance: Plants of the new *Papaver* have been observed to tolerate temperatures from −25 to 40° C.

It is claimed:

1. A new and distinct cultivar of *Papaver* plant named 'Matador', as illustrated and described.

* * * * *

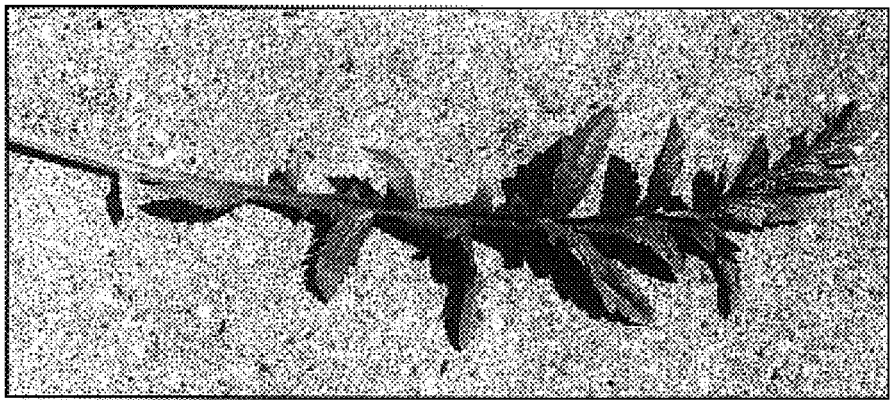

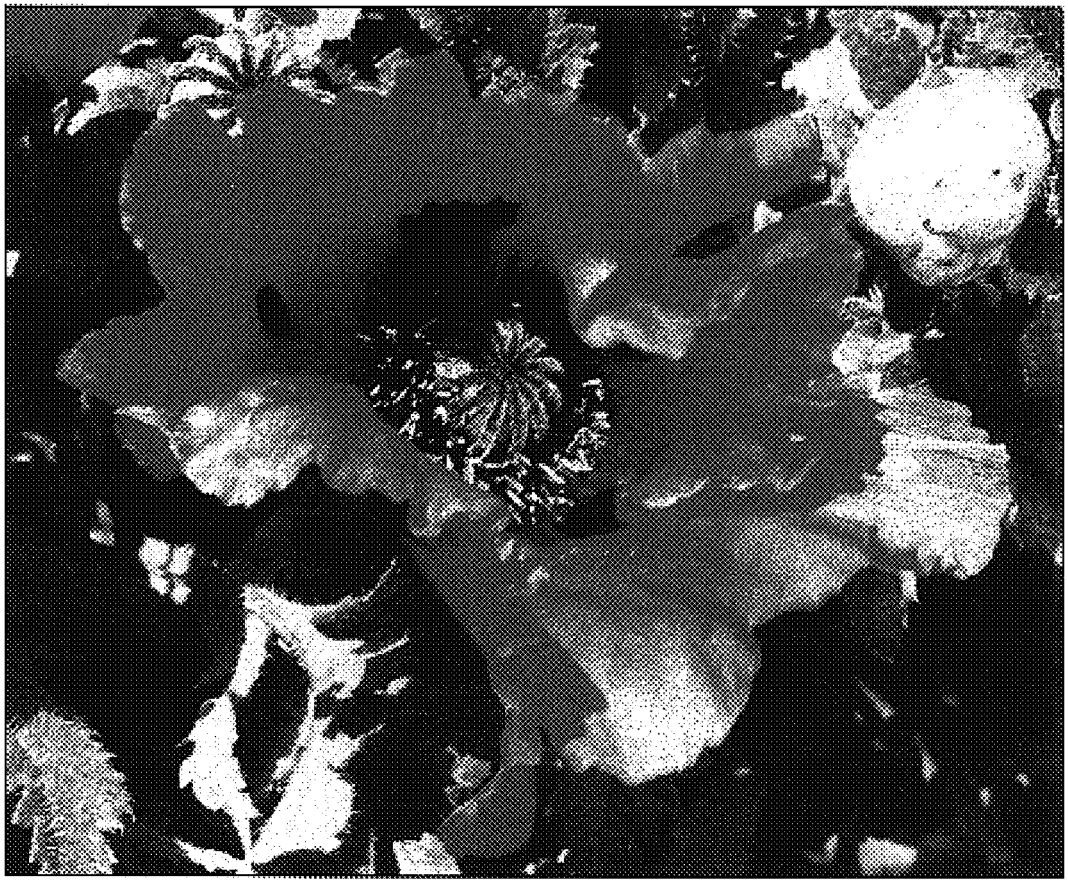
'Matador'